(12) United States Patent
Kalkbrenner et al.

(10) Patent No.: US 10,459,208 B2
(45) Date of Patent: Oct. 29, 2019

(54) MICROSCOPE AND METHOD FOR HIGH-RESOLUTION 3-D FLUORESCENCE MICROSCOPY

(71) Applicant: Carl Zeiss Microscopy GmbH, Jena (DE)

(72) Inventors: Thomas Kalkbrenner, Jena (DE); Ralf Wolleschensky, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 1341 days.

(21) Appl. No.: 14/371,816

(22) PCT Filed: Dec. 13, 2012

(86) PCT No.: PCT/EP2012/075464
§ 371 (c)(1),
(2) Date: Jul. 11, 2014

(87) PCT Pub. No.: WO2013/104483
PCT Pub. Date: Jul. 18, 2013

(65) Prior Publication Data
US 2015/0002632 A1    Jan. 1, 2015

(30) Foreign Application Priority Data

Jan. 11, 2012    (DE) .................. 10 2012 200 344

(51) Int. Cl.
*G02B 21/16*    (2006.01)
*G01N 21/64*    (2006.01)
(Continued)

(52) U.S. Cl.
CPC ............. *G02B 21/16* (2013.01); *G01N 21/64* (2013.01); *G01N 21/6402* (2013.01);
(Continued)

(58) Field of Classification Search
None
See application file for complete search history.

(56) References Cited

U.S. PATENT DOCUMENTS

2003/0230710 A1    12/2003    Wolleschensky et al.
2009/0237501 A1*    9/2009    Lemmer ............ G01N 21/6428
348/79
(Continued)

FOREIGN PATENT DOCUMENTS

DE    198 53 302 A1    5/2000
DE    100 63 276 A1    7/2002
(Continued)

OTHER PUBLICATIONS

Pavani, et al.;"Three-dimensional, single-molecule fluorescence imaging beyond the diffraction limit by using a double-helix point spread function";PNAS 2009;106(9):2995-2999.
(Continued)

*Primary Examiner* — David N Werner
(74) *Attorney, Agent, or Firm* — Duane Morris LLP

(57) ABSTRACT

In a sample, fluorescence emitters are repeatedly excited to emit fluorescence, and still images are produced of the sample by means of a microscope. At least a subset of the fluorescence emitters is isolated in each still image. The positions of the fluorescence emitters are localized in the still images with a location accuracy exceeding the optical resolution. A high-resolution composite image is generated therefrom. An adaptive mirror is arranged in the imaging beam path, and is adjusted in such a manner that it produces an astigmatism when at least one of the still images is produced. As a result, still images with astigmatism are captured. Depth position information for the fluorescence emitters is derived from the rotational asymmetry. The adaptive mirror is additionally adjusted in such a manner
(Continued)

that it does not produce any astigmatism when some of the still images are produced.

10 Claims, 2 Drawing Sheets

(51) Int. Cl.
    *G02B 21/36*     (2006.01)
    *G02B 27/58*     (2006.01)
    *G02B 21/04*     (2006.01)
    *G02B 21/00*     (2006.01)

(52) U.S. Cl.
    CPC ..... *G01N 21/6458* (2013.01); *G02B 21/0076* (2013.01); *G02B 21/04* (2013.01); *G02B 21/361* (2013.01); *G02B 21/365* (2013.01); *G02B 21/367* (2013.01); *G02B 27/58* (2013.01)

(56) References Cited

U.S. PATENT DOCUMENTS

| | | | |
|---|---|---|---|
| 2011/0002530 A1* | 1/2011 | Zhuang | G01N 21/6428 382/154 |
| 2011/0170180 A1 | 7/2011 | Turner et al. | |
| 2012/0224034 A1 | 9/2012 | Kalkbrenner | |
| 2013/0088776 A1* | 4/2013 | Nakayama | G01N 21/6458 359/381 |
| 2013/0302905 A1 | 11/2013 | Kalkbrenner et al. | |

FOREIGN PATENT DOCUMENTS

| | | |
|---|---|---|
| DE | 10 2006 021 317 B3 | 10/2007 |
| DE | 10 2009 043 744 A1 | 3/2011 |
| DE | 10 2009 060 490 A1 | 6/2011 |
| JP | 2004-102225 A | 4/2004 |
| JP | 2011-508214 A | 3/2011 |
| JP | 2011-231234 A | 11/2011 |
| JP | 2014-501915 A | 1/2014 |
| WO | WO 2006/127692 A2 | 11/2006 |
| WO | WO 2009/085218 A1 | 7/2009 |
| WO | WO 2011/152523 A1 | 12/2011 |

OTHER PUBLICATIONS

Shtengel, Gleb, et al.; "Interferometric fluorescent super-resolution microscopy resolves 3D cellular ultrastructure"; PNAS 2009; 106(9):3125-3130.
Toprak, Erdal, et al.; "Three-Dimensional Particle Tracking via Bifocal Imaging", NANO Letters 2007; 7(7):2043-2045.
Juette, Manuel F., et al.; "Three-dimensional sub-100 nm resolution fluorescence microscopy of thick samples"; Nature Methods 2008; 5(6):527-529.
Huang, Bo, et al.; "Three-Dimensional Super-Resolution Imaging by Stochastic Optical Reconstruction Microscopy"; Science 2008; 319:810-813 and Supporting Online Material.
Lew, et al.;"In vivo Three-Dimensional Superresolution Fluorescence Tracking using a Double-Helix Point Spread Function"; Proceedings of SPIE 2010; 7571:75710Z-1-75710Z13.
Baddeley, et al.; "4D Super-Resolution Microscopy with Conventional Fluorophores and Single Wavelength Excitation in Optically Thick Cells and Tissues";PLoS ONE 2011;6(5):1-10.
Bourgenot C., et al.; "Adaptive Optics for Wide-Field Microscopy"; Proceedings of SPIE 2011; 7904:790414-1-790414-7.
Izeddin, Ignacio, et al.; "PSF shaping using adaptive optics for three-dimensional single-molecule super-resolution imaging and tracking"; Optics Express 2012; 20(5):4957-4967.
www.bostonmicromachines.com/light-modulator.htm.
www.imagine-optic.com.
http://en.wikipedia.org/wiki/Deformable_mirror.
Japanese Office Action dated Dec. 6, 2016 with English translation.

\* cited by examiner

MICROSCOPE AND METHOD FOR HIGH-RESOLUTION 3-D FLUORESCENCE MICROSCOPY

RELATED APPLICATIONS

The present application is a U.S. National Stage application of International PCT Application No. PCT/EP2012/075464 filed on Dec. 13, 2012 which claims priority benefit of German Application No. DE 10 2012 200 344.4 filed on Jan. 11, 2012, the contents of each are incorporated by reference in their entirety.

FIELD OF THE INVENTION

The invention relates to a method for high-resolution 3D localization microscopy, wherein fluorescence emitters in a sample are repeatedly excited to emit fluorescence, and still images are produced of the sample by means of a microscope having an imaging beam path and a focal plane, wherein the fluorescence emitters are stimulated to emit fluorescence in such a manner that at least a subset of the fluorescence emitters is isolated in each still image, in such a manner that the images of these fluorescence emitters can be separated within the optical resolution in the still images. The positions of the fluorescence emitters, in the resulting still images, are localized from the images of the isolated fluorescence emitters, with a location accuracy exceeding the optical resolution. A high-resolution composite image is generated therefrom. An adaptive mirror is arranged in the imaging beam path of the microscope, and produces an astigmatism when the still images are produced. As a result, still images with astigmatism are captured. In these, the images of fluorescence emitters positioned above the focal plane have a first rotational asymmetry as a result of distortion in a first direction, and the images of fluorescence emitters positioned below the focal plane have a second rotational asymmetry as a result of distortion in a second direction, wherein depth position information for the fluorescence emitters is derived from the rotational asymmetry.

BACKGROUND OF THE INVENTION

The invention further relates to a fluorescence microscope for the three-dimensional imaging of a sample with a location accuracy beyond the optical resolution, wherein the fluorescence microscope has: an illumination device which is designed for the purpose of repeatedly exciting fluorescence emitters in the sample to emit fluorescence, an imaging device having an imaging beam path with the optical resolution, designed for the purpose of producing still images of the sample at the optical resolution, and a control device which is designed for the purpose of controlling the illumination device and the imaging device in such a manner that multiple still images of the sample are produced. The fluorescence emitters are excited to emit fluorescence in such a manner that at least a subset of the fluorescence emitters in each still image is isolated in such a manner that the images of these fluorescence emitters can be separated in the still images within the optical resolution. The control device is also designed for the purpose of localizing the positions of the isolated fluorescing fluorescence emitters in the generated still images with a location accuracy exceeding the optical resolution, and generating a high-resolution composite image therefrom. An astigmatic element which produces an astigmatism when the still images are produced, is provided such that astigmatic still images are thereby captured. The images of fluorescence emitters lying above the focal plane have a first rotational asymmetry as a result of distortion in a first direction, and the images of fluorescence emitters positioned below the focal plane have a second rotational asymmetry as a result of distortion in a second direction. The control device is designed for the purpose of deriving depth position information for the fluorescence emitters from the rotational asymmetry.

Various different methods have been developed in the prior art to overcome the diffraction limit in microscopy. A method, abbreviated as PALM (photo-activated light microscopy), is known from WO 2006/0127692 and DE A1, which uses a marking substance to image a sample, wherein said marking substance can be activated by means of optical radiation. The marking substance can only emit specific fluorescent radiation in the activated state. Inactivated molecules of the marking substance do not emit fluorescence radiation—or at least no noticeable fluorescence radiation, even after radiation with excitation light. For this reason, the excitation light is generally termed the switching signal. In the PALM method, the switching signal is applied in such a manner that at least some of the activated marking molecules are spaced apart from neighboring, activated marking molecules in such a manner that they are separated when viewed on the scale of the optical resolution of the microscope, or can be subsequently separated by image processing methods. In this case, one says that a subset of the fluorescence emitters have been isolated. After the fluorescence has been captured, the center of the radiation distribution for these isolated emitters is determined, said distribution being the result of the limit of the resolution. From this, it is possible to calculate the position of the molecules with higher precision than the optical resolution actually allows. This process is termed localization. The enhanced resolution resulting from a computational determination of the nucleus of the diffraction distribution is also termed "super resolution" in the technical literature in English. This resolution requires that at least a subset of the activated marking molecules in the sample can be differentiated—that is, isolated—at the optical resolution. Then, their position can be determined with a higher precision, and they can be localized.

To isolate individual fluorescence markers, the PALM principle exploits statistical effects. For a fluorescence marker which can be stimulated to emit fluorescence after receiving the switching signal at a given intensity, it is possible to adjust the intensity of the switching signal so that the probability of activating fluorescence markers present in a given area of the sample is so small that there is a sufficient number of sub-regions in which only fluorescence markers which can be differentiated within the optical resolution emit fluorescence.

The PALM principle has been further advanced with regards to the activation of the molecule which is targeted for detection. By way of example, for molecules which have a long-lived non-fluorescing state and a short-lived fluorescing state, a separate activation using activation light which is different in spectrum from the excitation light is not at all necessary. Rather, the sample is first illuminated with high-intensity excitation light in such a manner that the overwhelming majority of the molecules are brought into the long-lived state where fluorescence is not possible (e.g. a triplet state). The remaining molecules which are still fluorescing are thereby isolated with respect to the optical resolution.

It is also noted that the PALM principle has also been denoted in the technical literature with other abbreviations, such as STORM, for example. In this description, the abbreviation PALM is used for all microscope-based imaging which achieves a localizing resolution beyond the optical resolution of the apparatus being used, by first isolating fluorescent molecules and then localizing the same. The PALM method has the advantage that it is not necessary to have high localizing resolution for the illumination. A simple wide-field illumination is possible.

The PALM principle requires that many still images of the sample are captured, each containing subsets of isolated molecules. In order to image the sample as a whole, the number of the individual images in total must be sufficient to ensure that as many molecules as possible are at least present one time in one subset. The PALM method therefore regularly requires a plurality of still images, which requires a certain period of time for a composite image to be captured. A significantly complex calculation process is involved because a plurality of molecules must be localized in each still image. Large amounts of data are involved.

This location accuracy is only achieved laterally, by the localization in still images—that is, in a plane to which the image plane of the camera is functionally assigned. The methods are therefore limited in this respect to a two-dimensional analysis of a sample. The PALM principle is therefore combined with a TIRF excitation, which ensures that only fluorophores in a thin layer of the sample emit fluorescence.

Approaches are also known in the prior art for the localization of luminescing fluorescence markers in the third spatial dimension, which is the depth dimension with respect to the imaging of the sample. The term "depth dimension" in this case means the direction along the incident light path—that is, along the optical axis.

The publication Pavani et al., PNAS 106, page 2995, 2009, suggests modifying the point spread function in the imaging process to give a double helix structure, by means of a spatial phase modulator. The one-dimensional images of individual, luminescing fluorescence markers then become double spots. Their depth position is encoded in the angular orientation of the common axis of the double spots.

According to the publication by Shtengel, et al, PNAS 106, page 3125, 2009, photons which are emitted by the fluorescing fluorescence markers are caused to interfere with themselves. For this purpose, two lenses which are assembled in the 4π configuration are used to simultaneously observe the fluorescing fluorescence markers. By means of a special, 3-way beam splitter, the radiation is made to achieve interference. Each of the resulting images is detected by a camera, and the proportional intensities of the three-point images provide information on the depth positions.

The publications Toprak et al., Nanolet. 7, pages 3285-3290, 2007, and Juette et al., Nature Methods 5, page 527, 2008, describe an approach wherein a 50/50 beam splitter is installed in the imaging beam path and splits the image of the sample into two partial images which can be detected independently. In addition, an optical path length difference is inserted into one of the partial beam paths obtained in this manner, downstream of the beam splitter, in such a manner that the two object planes are produced from the two partial beam paths, which are spaced apart from each other in the z—that is, depth—dimension by approximately half of the minimum optical resolution (for example 700 nm), or by the whole minimum optical resolution. The depth position of fluorescence markers which lie between these two planes is then obtained from subtraction of the two partial images of the same fluorescence marker, or by a corresponding fitting of a three-dimensional point spread function. DE 102009060490 also uses this approach, providing further evidence for three-dimensional high-resolution. The method requires two highly resolved partial images and a precise adjustment of the beam paths and calibration measurements in order to achieve a superimposition of these two partial images with sub-pixel precision. In addition, the two partial images of a fluorescence marker generally have a different shape because the lateral expansion of the point spread function of a system being imaged changes according to the position of the object plane being observed.

The publication B. Huang et al., Science 319, page 810, 2008 discloses a method and a microscope of the type named above. A weak cylindrical lens lies in the imaging beam path, thereby leading to a specific astigmatic distortion. As a result, the image of the marker on the camera is elliptically distorted as soon as the marker is positioned above or below the focal plane—that is, the symmetry point of the point spread function. The information on the depth position of the fluorescing fluorescence marker can be obtained from the orientation and the degree of the distortion. A disadvantage of this method is that the local environment and orientation of a molecular dipole can also lead to distortion of the image of the fluorescing fluorescence marker, and this distortion nevertheless has nothing to do with the depth position. Such fluorescing fluorescence markers therefore are assigned a false depth value, depending on their orientation.

SUMMARY OF THE INVENTION

The invention addresses the problem of advancing such a method, in such a manner that these deficiencies are avoided.

The problem is addressed according to the invention by a method for high-resolution 3D fluorescence microscopy, wherein a) fluorescence emitters in a sample are repeatedly excited to emit fluorescence, and still images are produced of the sample by means of a microscope having an imaging beam path and a focal plane, wherein the fluorescence emitters are stimulated to emit fluorescence in such a manner that at least a subset of the fluorescence emitters is isolated in each still image, in such a manner that the images of these fluorescence emitters can be separated within the optical resolution in the still images, b) in the resulting still images, the positions of the fluorescence emitters are localized from the images of the isolated fluorescence emitters, with a location accuracy exceeding the optical resolution, and a high-resolution composite image is generated therefrom, c) an adaptive mirror is arranged in the imaging beam path of the microscope, and is adjusted in such a manner that it produces an astigmatism when at least some of the still images are produced, thereby capturing still images with astigmatism, wherein the images of fluorescence emitters positioned above the focal plane have a first rotational asymmetry as a result of distortion in a first direction, and the images of fluorescence emitters positioned below the focal plane have a second rotational asymmetry as a result of distortion in a second direction, wherein depth position information for the fluorescence emitters is derived from the rotational asymmetry, d) the adaptive mirror is additionally adjusted in such a manner that it does not produce any astigmatism when at least some of the still images are produced, such that non-astigmatic still images are captured, and e), rotationally asymmetric images of fluorescence emitters are detected in the non-astigmatic still images, and in the derivation process for the depth position information in the astigmatic still images, these fluorescence emitters are subjected to a depth position correction, or are suppressed.

The problem is further addressed by a fluorescence microscope for the three-dimensional imaging of a sample with a location accuracy beyond the optical resolution, having: an illumination device which is designed for the purpose of repeatedly exciting fluorescence emitters in the sample to emit fluorescence, an imaging device having an imaging beam path with the optical resolution, designed for the purpose of producing still images of the sample at the optical resolution, a control device which is designed for the purpose of controlling the illumination device and the imaging device in such a manner that multiple still images of the sample are produced, wherein the fluorescence emitters are excited to emit fluorescence in such a manner that at least a subset of the fluorescence emitters in each still image is isolated in such a manner that the images of these fluorescence emitters can be separated in the still images within the optical resolution, wherein the control device is also designed for the purpose of localizing the positions of the isolated fluorescing fluorescence emitters in the generated still images with a location accuracy exceeding the optical resolution, and generating a high-resolution composite image therefrom, the imaging device has an adaptive mirror, the control device is designed for the purpose of adjusting the adaptive mirror in such a manner that the same produces an astigmatism when at least some of the still images are produced, such that astigmatic still images are thereby captured, wherein the images of fluorescence emitters lying above the focal plane have a first rotational asymmetry as a result of distortion in a first direction, and the images of fluorescence emitters positioned below the focal plane have a second rotational asymmetry as a result of distortion in a second direction, wherein the control device is designed for the purpose of deriving depth position information for the fluorescence emitters from the rotational asymmetry, and the control device is designed for the purpose of additionally adjusting the adaptive mirror in such a manner that it does not produce any astigmatism when at least some of the still images are produced, such that non-astigmatic still images are captured, and the control device is designed for the purpose of detecting rotationally asymmetric images of fluorescence emitters in the non-astigmatic still images, and of subjecting these fluorescence emitters to a depth position correction, or suppressing the same, in the derivation process for the depth position information in the astigmatic still images.

The invention uses an adaptive mirror as an essential element for advancing the depth resolution concept based on astigmatism as described by Huang et al. This means a mirror with a mirror surface curvature which can be modified. Such mirrors are known per se in the prior art. To date, both astigmatic still images from which depth information is obtained, and also non-astigmatic still images—which are utilized for the purpose of correcting the depth information—have been generated by means of the adaptive mirror. A fluorescence emitter implementing a dipole already has an innately distorted point image, and would be wrongly assigned a false depth position in the astigmatic still image. Here, this emitter is suppressed during the depth analysis, or its point image distortion which is visible in the non-astigmatic still image is used as a starting point for obtaining the depth information. This can be performed by using the distorted starting shape of the point image known from the non-astigmatic still image as a zero-position indication. The non-astigmatic still images thereby provide the reference shape of the images of the fluorescence emitters for the focal plane (zero-position depth information).

The error-correction achieved according to the invention with respect to the fluorescence emitters, the same having a non-rotationally symmetric point image per se—meaning regardless of an astigmatism introduced additionally to the depth analysis—makes it further possible to reliably follow such fluorescence emitters in a so-called tracking process for applications where dynamic processes are being resolved.

The work area of the depth resolution can be adapted by means of the adaptive mirror to different requirements and/or to the use of different lenses, by adjusting the degree of the astigmatism. The depth resolution can also be switched off for certain applications without any problem, by adjusting the adaptive mirror in such a manner that it does not cause any astigmatism. The use of a mirror also has the advantage of avoiding a potential chromatic aberration, as could appear in a cylindrical lens.

Mirrors with segmented surfaces, or continuous, so-called membrane mirrors, are particularly suitable as the adaptive mirror. These are currently known to a person skilled in the art, for example from the publication www.bostonmicromachines.com/light-modulator.htm or www.imagine-optic.com. Additionally, an overview of adaptive mirrors is found at http://cn.wikipedia.org/wiki/Deformable_mirror.

The adaptive mirror is preferably combined with a wave front sensor which detects the wave front of the radiation which has been reflected by the mirror. In this way, imaging errors of the microscope, or imaging errors caused by the sample, are optionally corrected. Moreover, the focal plane can be displaced within certain boundaries without any problem, without the need to adjust the microscope lens. In this way, it is possible to prevent mechanical disturbances of the sample resulting from the movement of the microscope lens.

The generation of the non-astigmatic still images can take place intermittently between the generation of the astigmatic still images. The adaptive mirror is then inserted between a surface shape which is known to produce astigmatism, and a surface shape which does not cause astigmatism. The advantage of this approach is that the different still images are automatically perfectly aligned with each other, because they are captured by the same camera.

In addition, the non-astigmatic still image, which is used for the purpose of depth correction, can be generated less frequently according to the conditions of the application—for example if a sample is used for which distortions of images of the fluorescence emitters resulting from dipoles are expected and/or are not expected.

For processes which run quickly, wherein a quick image capture is desirable, the adaptive mirror can be used as a beam splitter in the imaging beam path, as an alternative to the intermittent non-astigmatic operation mode, such that the adaptive mirror produces two laterally separate still images. These can be, by way of example, imaged on different sub-regions of one and the same camera. As a result, it is possible to image the non-astigmatic still image and the astigmatic still image on the image field of one camera at the same time—that is, next to each other. The amount of effort needed for alignment, to make precise assignments of the precise still images, remains very minimal in this case, because only the adjustable adaptive mirror functions to split the beam. The desired adjustment with sub-pixel precision can be effected simply and without great effort by means of a suitable control of the adaptive mirror.

If a camera with two image field regions is used, both still images can be available simultaneously.

The degree of astigmatism which is introduced has an effect on the distortion of the point images of the fluorescence emitters. A strong astigmatism leads to a strong distortion, meaning that fluorescence emitters which lie a relatively short distance above or below the focal plane are comparatively strongly distorted. A high depth resolution is the result. If, in contrast, the astigmatism is made weaker, the same distortion of the point images is only achieved at greater distances from the focal plane. As a result, the captured depth range is greater. Therefore, it is possible to easily switch between the inherently contradictory requirements of depth resolution and [good] captured depth range using a suitable control of the adaptive mirror.

The "image of a fluorescence emitter" should be understood to mean the generally diffraction-limited point image thereof.

It should be understood that the features discussed above and explained below can be used not only in the combinations given, but also in other combinations or alone, without departing from the scope of the present invention. Where method features are mentioned in this description, they are implemented in the operation of the microscope by an accordingly designed control device. Similarly, a disclosure of functional features of the control device also applies as a description of corresponding features—e.g. steps—of the method.

BRIEF DESCRIPTION OF THE DRAWINGS

The invention is described in greater detail below with reference to the attached drawings, which also disclose features which are essential to the invention, wherein.

DESCRIPTION OF THE EMBODIMENTS

Figure 1:
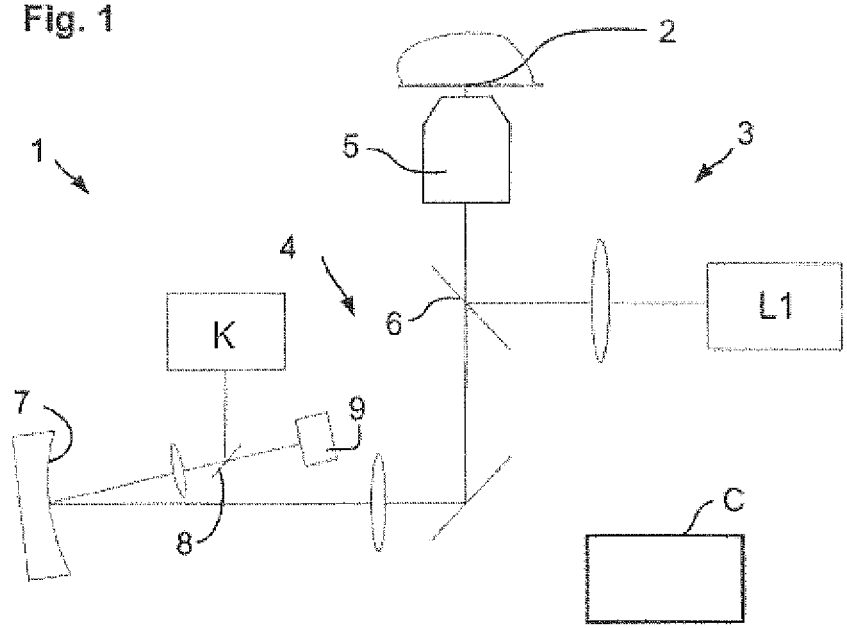
FIG. 1 shows a schematic illustration of a microscope for depth-resolving and high-resolution fluorescence microscopy.

FIG. 1 schematically shows a fluorescence microscope 1, the operation of which is controlled by a control device C. It is connected to the elements and/or components of the microscope 1 via connections which are not shown. The microscope 1 is configured for the purpose of performing fluorescence microscopy according to the PALM principle, etc. It comprises an imaging beam path 3, and an imaging beam path 4. These illuminate a sample 2 and image the fluorescing sample via a common lens 5. The imaging beam path 3 is combined with the imaging beam path 4 via a beam splitter 6 which typically has a dichroic design, such that the illumination light from the imaging beam path 3 falls on the sample through the lens 5, and the imaging of the sample also occurs through the lens 5. The imaging beam path 3 can have multiple spectral channels. By way of example, only one laser source L1 is illustrated in the drawing in FIG. 1. The imaging beam path illuminates the sample in such a manner that fluorescence is excited in the sample 2. According to the design of the [implemented] PALM principle, another excitation beam source can be additionally coupled into the imaging beam path 3.

The sample 2 emits fluorescence, and the image of the fluorescing sample 2 is relayed in the imaging beam path 4 to a high-resolution camera K. The resolution of the lens 5, the imaging beam path 4, and the camera K is selected such that a diffraction-limited point image of a single fluorescence emitter falls on multiple pixels. This enables the localization, as required for the PALM principle illustrated above, of a fluorescence emitter with a lateral location accuracy which exceeds the optical resolution of the microscope 5 and the imaging beam path 4.

Of course, the microscope 1 can also be designed with multiple color channels. Then, multiple cameras are included in the imaging beam path 4, and are coupled into the beam path via suitable beam splitters.

The imaging beam path 4 includes—in additional optical elements which are not indicated in greater detail, which are not further characteristic for the microscope 1 and are otherwise conventional technical devices—an adaptive mirror 7 with a curved mirror surface which is part of the imaging beam path 4. It bundles the rays of the fluorescing sample 2 in the direction of the camera K.

The adaptive mirror is controlled by the control device C which adjusts the geometry of the mirror surface. A wave front sensor 9 which is switched via a beam splitter in the imaging beam path 4 serves the purpose of making it possible for the control device C to detect the current mirror function as precisely as possible. In this way, it increases the precision, but is not absolutely necessary.

The control device C controls the microscope 1 in such a manner that the PALM principle is executed. The sample 2 is therefore illuminated by the imaging beam path 2 in such a manner that fluorescence emitters in the sample 2 are isolated—meaning that they can be separated within the optical resolution. A plurality of still images is captured, each of which contain isolated, different subsets of the fluorescence emitters in the sample 2. In the still images, then, the position of each isolated fluorescence emitter is determined with high precision by the control device C, by means of known mathematical algorithms, such that a location accuracy which exceeds the optical resolution of the imaging is achieved. This is termed super-resolution in the literature.

As is schematically shown in FIG. 1, the sample 2 comprises a volume which extends perpendicular to the incident direction of the illumination beam, and/or perpendicular to the imaging process. In order to be able to derive depth information for isolated fluorescence emitters at this point, the control device C adjusts the adaptive mirror 7 in such a manner that it produces a light astigmatism. The curvature of the surface of the mirror 7 is therefore no longer a rotational paraboloid. Rather, it has different parabolic shapes in two sectional planes lying perpendicular to each other. As a result, only those fluorescence emitters which lie exactly in the focal plane of the optical imaging process do not have a diffraction disk which is distorted by this astigmatism. Fluorescence emitters which lie above the focal plane are distorted elliptically in a first direction. Fluorescence emitters which lie below the focal plane are distorted elliptically in a second direction which is oriented perpendicular to the first.

Figure 2:
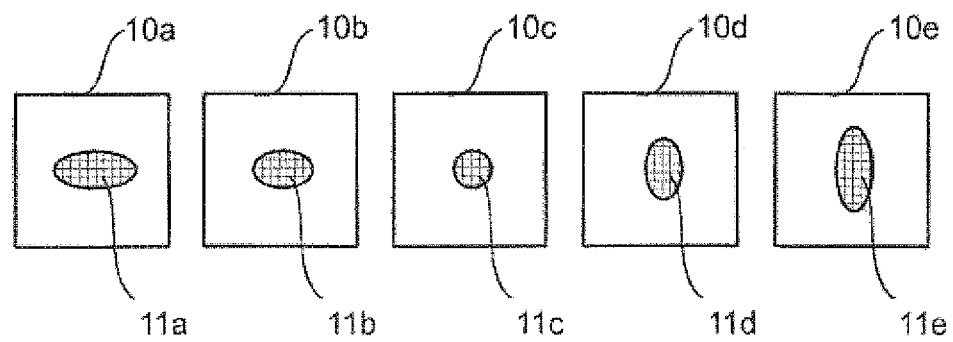
FIG. 2 shows a schematic illustration of different point images of a fluorescence emitter, for the purpose of clarifying the depth resolution.

This is shown in FIG. 2, in which five detail sections 10a-10e of still images are illustrated. The section 10c relates to a fluorescence emitter which lies exactly in the focal plane. As can be seen, its image 11c is circular. The images 11b and 11a of fluorescence emitters which lie above the focal plane are elliptically distorted—horizontally in the schematic illustration in FIG. 2. The degree of the distortion increases the farther the fluorescence emitter is from the focal plane. Fluorescence emitters which, in contrast, are below the focal plane, are distorted in a direction which is perpendicular thereto, as the images 11d and 11e show. Here as well, the degree of the distortion increases with distance from the focal plane.

In the still images, the astigmatism of the adaptive mirror 7 therefore produces a rotational asymmetry, the degree of which depends on the distance from the focal plane, and the direction of which depends on whether the fluorescence emitter is above or below the focal plane.

The control device 10 at this point uses the deliberately introduced distortion to detect the depth position for each isolated fluorescence emitter. For this purpose, the control device C evaluates the degree of the distortion as well as the direction of the distortion.

Figure 3:
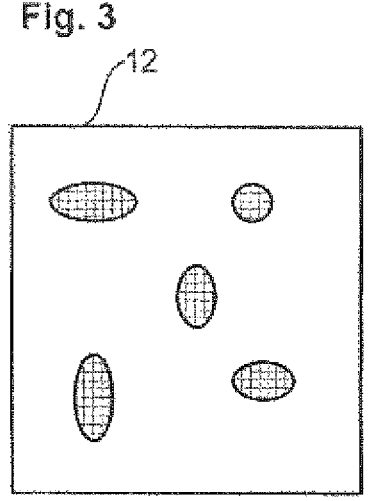
FIGS. 3 and 4 show still images which are produced when the microscope in FIG. 1 is operated for depth resolution.

FIG. 3 shows a still image 12 in an exemplary manner, wherein the same is affected by astigmatism as a result of the corresponding adjustment of the adaptive mirror 7. As can be seen, it is possible to easily determine the depth position from the direction and degree of the rotational asymmetry when the astigmatism produced by the adaptive mirror 7 is taken into account. This can be performed by means of corresponding calculations, or—in a particularly simple manner—by a calibration on a sample with a known depth structure.

As already noted in the general portion of the description, the degree of the distortion of course depends on the degree of the adjusted astigmatism. With suitable variation of the controlling procedure of the adaptive mirror 7, the detected depth range and the depth resolution can consequently be easily adjusted, wherein these two values have an inverse relationship to each other.

Fluorophores which act as dipoles can at this point have a rotationally asymmetric, diffraction-limited point image even in the focal plane if the dipole is tilted with respect to the optical axis. If the control device C would analyze the images of such fluorophores for their rotational asymmetry, false depth position information would result.

Figure 4:
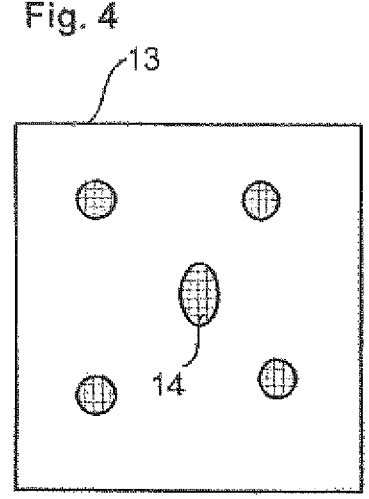

In order to prevent a false evaluation of fluorescence emitters which show a non-rotationally symmetric point image per se, the control device C makes an intermittent adjustment to the adaptive mirror 7 which does not introduce any astigmatism into the imaging beam path 4. As a result, a still image 13 is obtained, as shown in FIG. 4. In this case, all fluorescence emitters which have a rotationally symmetric point image per se also appear as circular diffraction disks. However, a fluorescence emitter which has a non-rotationally symmetric point image 14 as a result of the explained dipole effect or local disturbances can be recognized in the non-astigmatic still image 13 by a non-rotationally symmetric diffraction disk.

The control device C at this point takes this point image 14 as the starting point for the determination of the distortion for the depth position analysis.

In this case, it is possible that the specific fluorescence emitters which produce images which do not fulfill certain requirements of rotational symmetry are filtered from the astigmatic still image 13, and also that a suitable correction is carried out for these fluorescence emitters and/or the images thereof during the depth position determination, or these fluorescence emitters are suppressed as regards the depth position evaluation. Similarly, for each fluorescence emitter, the geometry of the point image produced in the still image without added diffraction can be analyzed, and this geometry can be used as the reference point for the focal position (corresponding to the depth position z=0).

Above, it was explained that the control device C intermittently switches the adaptive mirror 7 between a state which introduces astigmatism and a state in which no additional astigmatism is introduced into the imaging beam path 4. The still images 12 and 13 are therefore taken intermittently. This has the advantage that the still images are precisely aligned with each other, and the complete image field of the camera K can be exploited.

Figure 5:
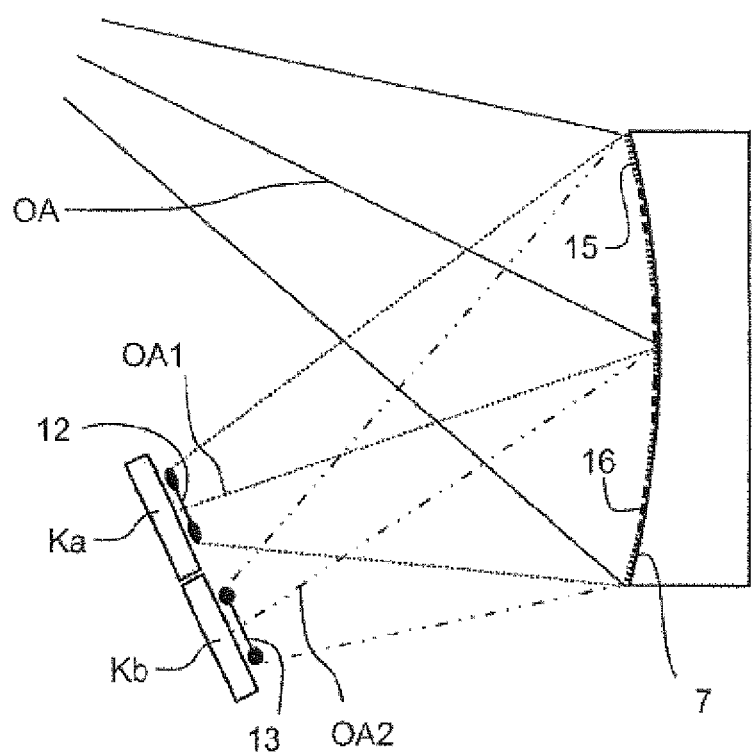
FIG. 5 shows a schematic illustration of a modification of the imaging beam path of the microscope in FIG. 1.

FIG. 5 schematically shows a modification of the imaging beam path 4 with respect to the adaptive mirror 7 and the camera K, wherein the adaptive mirror 7 functions as a beam splitter which images the still image 12 with added diffraction next to the image 13 with added diffraction, on two image regions Ka and Kb of the camera (or two independent cameras). Further imaging elements such as lenses, etc. can be used in this case, but are not included in the illustration in FIG. 5, to allow better understanding. By way of example, the adaptive mirror 7 is adjusted in such a manner that it has mirror surface segments 15 which deflect the optical axis OA in a first direction. Mirror surface segments 16 interlaced therewith deflect the optical axis OA in a second direction. In this case, the first direction is an optical axis OA1 which is functionally assigned to the camera image region Ka, and the second direction corresponds to an optical axis OA2 which is functionally assigned to the camera image region Kb. The corresponding peripheral rays for the imaging by the first mirror surface segment 15 are sketched with a dotted line in FIG. 5, as is the optical axis OA1, while the peripheral rays and the optical axis OA2 directed through the mirror surface segment 16 to the camera image region Kb are drawn with a dashed line.

For the beam-splitting function of the adaptive mirror 7, it is advantageous if the same is positioned near to and/or in a pupil of the imaging beam path. In this case, the mirror surface can particularly be divided into identical surface fractions for the mirror surface segments 15 and 16. The control and/or design of the adaptive mirror 7 is then particularly simple.

If the mirror is arranged outside of the pupil (for example with a deviation of more than 10% of the focal length), the interlaced mirror surface segments 15 and 16 must be distributed spatially over the mirror surface, taking into account the precise imaging, in order to achieve a desired beam splitting factor (for example 1:1). This is also possible, but requires a more complex control and/or design.

The mirror surface segments 15 further produce astigmatism in the generated still image 12. The adaptive mirror 7 is consequently adjusted in such a manner that it not only effects an image division, but also in such a manner that astigmatism is introduced into a still image.

The beam splitting effect of the adaptive mirror 7 operated in this manner has the advantage that the astigmatic still image 12 is available at the same time as the non-astigmatic still image 13. The differences in the distortion of these images are schematically indicated in FIG. 3 by circles and/or ellipses. The simultaneous availability of the still images 12 and 13 makes it particularly easy to use the point-image geometry of each fluorescence emitter as the starting point for the z-position determination in the astigmatic still image 12.

The description above makes the assumption, for reasons of simplicity, that the adaptive mirror 7 is the only element which deliberately introduces astigmatism into the imaging beam path 4. This, of course, does not rule out that the imaging process has a certain astigmatism due to other optical effects. If one desires to suppress this phenomenon, the optional implementation using a beam splitter 8 and wave front sensor 9 is advantageous because the adaptive mirror can then be used for the purpose of eliminating an undesired systemic astigmatism of the imaging beam path 4. The terms "non-astigmatic" and "astigmatic" therefore refer to deliberately introduced and/or suppressed astigmatism which serves the purpose allowing depth resolution. Of course, a correction of other imaging errors of the entire imaging system, and optionally of the sample, can also be performed by means of the adaptive mirror. The wave front sensor 9 also simplifies this.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed is:

1. A method for high-resolution 3D fluorescence microscopy, comprising
   (a) repeatedly exciting fluorescence emitters in a sample to emit fluorescence, and producing still images of the sample by means of a microscope having an imaging beam path with an optical resolution and a focal plane, said fluorescence emitters being stimulated to emit fluorescence in such a manner that at least a subset of the fluorescence emitters is isolated in each still image, so that the images of these fluorescence emitters can be separated in the still images within the optical resolution,
   (b) localizing the positions of the fluorescence emitters from the images of the isolated fluorescence emitters in the resulting still images, with a location accuracy exceeding the optical resolution, and generating a high-resolution composite image therefrom,
   (c) arranging an adaptive mirror in the imaging beam path of the microscope, and adjusting said mirror in such a manner that it produces an astigmatism when at least some of the still images are produced, thereby capturing still images with astigmatism, said images of the fluorescence emitters positioned above the focal plane having a first rotational asymmetry as a result of distortion in a first direction, and the images of fluorescence emitters positioned below the focal plane having a second rotational asymmetry as a result of distortion in a second direction, wherein depth position information for the fluorescence emitters is derived from the rotational asymmetry,
   (d) further adjusting said adaptive mirror in such a manner that it does not produce any astigmatism when at least some of the still images are produced, such that non-astigmatic still images are captured, and
   (e) detecting rotationally asymmetric images of fluorescence emitters in the non-astigmatic still images, and in the derivation process for the depth position information in the astigmatic still images these fluorescence emitters are either subjected to a depth position correction, or are suppressed.

2. The method according to claim 1, wherein the non-astigmatic still images produced in step (d) are carried out intermittently between step (c), in which astigmatic still images are produced.

3. The method according to claim 2, wherein said adaptive mirror is adjusted in such a manner that it images an astigmatic still image on a first image capture region and a non-astigmatic still image on a second image capture region at the same time.

4. The method according to claim 1, wherein in step (e), the images of the fluorescence emitters in the non-astigmatic still images are used as the starting point for the determination of the rotational asymmetry, for the depth position correction in the derivation of the depth position information.

5. The method according to claim 1, wherein a degree of astigmatism produced by the adaptive mirror is adjusted in order to adjust a depth resolution.

6. A fluorescence microscope for three-dimensional imaging of a sample with a location accuracy exceeding the optical resolution, comprising:
   an illumination device designed for repeatedly exciting fluorescence emitters in the sample to emit fluorescence,
   an imaging device having an imaging beam path with the optical resolution for producing still images of the sample at the optical resolution,
   a control device for controlling the illumination device and the imaging device in such a manner that multiple still images of the sample are produced, said fluorescence emitters being excited to emit fluorescence in such a manner that at least a subset of the fluorescence emitters in each still image is isolated so that the images of these fluorescence emitters can be separated in the still images within the optical resolution
   said control device being designed for localizing the positions of the isolated fluorescing fluorescence emitters in the generated still images with a location accuracy exceeding the optical resolution, and of generating a high-resolution composite image therefrom,
   the imaging device having an adaptive mirror,
   the control device for adjusting the adaptive mirror being designed to produce an astigmatism when at least some of the still images are produced, such that astigmatic still images are thereby captured, wherein the images of fluorescence emitters lying above the focal plane in said still images have a first rotational asymmetry as a result of distortion in a first direction, and the images of fluorescence emitters positioned below the focal plane have a second rotational asymmetry as a result of distortion in a second direction, wherein the control device is designed for the purpose of deriving depth position information for the fluorescence emitters from the rotational asymmetry,
   said control device additionally adjusting the adaptive mirror in such a manner that it does not produce any astigmatism when at least some of the still images are produced, such that non-astigmatic still images are captured, and
   the control device being designed for detecting rotationally asymmetric images of fluorescence emitters in the non-astigmatic still images, and of subjecting these fluorescence emitters either to a depth position correction, or suppressing the same, in the derivation process for the depth position information in the astigmatic still images.

7. The fluorescence microscope according to claim 6, wherein the control device for adjusting the adaptive mirror is designed in such a manner that non-astigmatic still images are produced intermittently between astigmatic still images.

8. The fluorescence microscope according to claim 6, wherein said imaging device has a first image capture region and a second image capture region, and the control device is designed for the purpose of adjusting the adaptive mirror in such a manner that it images an astigmatic still image on a first image capture region and a non-astigmatic still image on a second image capture region at the same time.

9. The fluorescence microscope according to claim 6, wherein said control device is designed for the purpose of using the images of the fluorescence emitters as the starting point for the determination of the rotational asymmetry, for the depth position correction in the derivation of the depth position information in the astigmatic still images.

10. The fluorescence microscope according to claim 6, wherein said control device is designed for the purpose of adjusting a degree of astigmatism produced by the adaptive mirror in order to adjust a depth resolution.

* * * * *

UNITED STATES PATENT AND TRADEMARK OFFICE
CERTIFICATE OF CORRECTION

PATENT NO. : 10,459,208 B2
APPLICATION NO. : 14/371816
DATED : October 29, 2019
INVENTOR(S) : Thomas Kalkbrenner and Ralf Wolleschensky Page 1 of 1

It is certified that error appears in the above-identified patent and that said Letters Patent is hereby corrected as shown below:

In the Specification

Column 2, Line 12   now reads: "microscopy), is known from WO 2006/0127692 and DE A1,"
should read -- microscopy), is known from WO 2006/0127692 and DE102006021317A1, --

Column 6, Line 25   now reads: "found at http://cn.wikipedia.org/wiki/Deformable_mirror."
should read -- found at http://en.wikipedia.org/wiki/Deformable_mirror. --

Signed and Sealed this
Tenth Day of December, 2019

Andrei Iancu
*Director of the United States Patent and Trademark Office*